United States Patent [19]

Shirai et al.

[11] Patent Number: 5,122,235
[45] Date of Patent: Jun. 16, 1992

[54] PROCESS FOR THE REMOVAL OF CHLOROPRENE FROM, 1,2-DICHLOROETHANE

[75] Inventors: Kenji Shirai, Takaishi; Seiji Nagae, Izumi; Tadashi Naito, Takaishi; Atsushi Shirai, Sennan, all of Japan

[73] Assignee: Mitsui Toatsu Chemicals, Incorporated, Tokyo, Japan

[21] Appl. No.: 555,497

[22] PCT Filed: Jul. 20, 1990

[86] PCT No.: PCT/JP90/00935
§ 371 Date: Aug. 10, 1990
§ 102(e) Date: Aug. 10, 1990

[51] Int. Cl.⁵ .................. B01D 3/00; C07C 17/38
[52] U.S. Cl. .................................. 203/28; 203/71; 203/73; 203/87; 203/98; 203/DIG. 9; 570/262
[58] Field of Search ............ 203/28, DIG. 6, 98, 203/DIG. 9, 87, 71, 73, 80; 570/262, 226

[56] References Cited

U.S. PATENT DOCUMENTS

| | | |
|---|---|---|
| 2,748,176 | 5/1956 | Morris ............... 570/262 |
| 2,752,297 | 6/1956 | Kleiman ............. 203/28 |
| 2,933,539 | 4/1960 | Hillard ............... 203/28 |
| 3,017,331 | 1/1962 | Campbell et al. ..... 203/28 |
| 3,397,120 | 8/1968 | Diana et al. ........ 203/28 |
| 3,476,955 | 11/1969 | Krekeler et al. ..... 570/226 |
| 3,548,014 | 12/1970 | Jacobowsky et al. .. 570/262 |
| 4,060,460 | 11/1977 | Smalley et al. ...... 570/262 |
| 4,145,367 | 3/1979 | Boozalis et al. ..... 570/262 |
| 4,188,347 | 2/1980 | Schmidhammer et al. 570/262 |
| 4,252,749 | 2/1981 | Campbell et al. ..... 570/262 |

Primary Examiner—Wilbur Bascomb, Jr.
Attorney, Agent, or Firm—Millen, White & Zelano

[57] ABSTRACT

Disclosed herein is a process for removing chloroprene by subjecting chloroprene-containing 1,2-dichloroethane to heat treatment at a temperature in the range of from the boiling point (85° C.) of 1,2-dichloroethane to the thermal cracking temperature (300° C.) of 1,2-dichloroethane. In particular, the process can be suitably applied to a liquid distillate from a low-boiling material separation column in a step in which 1,2-dichloroethane used as a raw material for production of vinyl chloride is purified by using a fractionation column.

10 Claims, 1 Drawing Sheet

PROCESS FOR THE REMOVAL OF CHLOROPRENE FROM 1,2-DICHLOROETHANE

DESCRIPTION

1. Technical Field

The present invention relates to a process for removing chloroprene which may be contained as an impurity in 1,2-dichloroethane. More specifically, this invention is concerned with a process for effectively removing chloroprene upon purification of 1,2-dichloroethane by distillation, which process can be applied to the production technology of vinyl chloride by thermal cracking of 1,2-dichloroethane.

2. Background Art

Production of vinyl chloride (hereinafter referred to as "VCM") by the thermal cracking of high-purity 1,2-dichloroethane (hereinafter referred to as "EDC"), namely, synthesis of VCM by the so-called thermal cracking process is industrially practiced on a large scale.

In a conventional process for the production of VCM, crude EDC obtained by direct chlorination or oxychlorination of ethylene is subjected to a purification step which uses a dehydrating column, a low-boiling material separation column and a high-boiling material separation column, thereby removing firstly water, then low-boiling impurities, and further high-boiling impurities to obtain purified EDC. The purified EDC is thereafter fed to a VCM-producing thermal cracker.

About 50-60% of the purified EDC is cracked in the thermal cracker, so that a cracked gas containing VCM and hydrogen chloride is obtained. This cracked gas is quenched and condensed, thereby separating and recovering hydrogen chloride and then VCM. A residue which has been obtained after the separation and recovery of hydrogen chloride and VCM contains, in addition to unreacted EDC, side reaction products formed during the thermal cracking. Unreacted EDC with the side reaction products contained therein (hereinafter called the "unreacted EDC") is subjected to the aforementioned purification process and is then fed again as purified EDC to the thermal cracker.

The side reaction products in unreacted EDC, however, include chloroprene as a low-boiling impurity.

Inclusion of chloroprene in EDC will lead to two serious problems.

Firstly, when chloroprene is contained in purified EDC to be fed to the thermal cracker, accelerated coking of cracking tubes and suppression to the cracking reaction will be observed. To avoid them, it is essential to control the content of chloroprene below 100 ppm in purified EDC which has an EDC content of 99% or higher.

Secondly, chloroprene is relatively prone to polymerization. When chloroprene is concentrated in a low-boiling material separation column in a purification process of unreacted EDC, it may be polymerized inside the column and may induce blocking of the column. It is therefore difficult to improve the efficiency of separation of chloroprene by increasing the degree of its concentration, so that the distillate is discharged out of the system while containing EDC at a relatively high concentration. It is thus difficult to improve the efficiency of separation of chloroprene in a purification process. Further, the inclusion of chloroprene results in a reduction in the unit of EDC. To avoid blocking of the low-boiling material separation column, it is necessary to control below 5 wt.% the concentration of chloroprene in vapor to be discharged from the top.

In the prior art, it has therefore been difficult to overcome problems such as blocking of the low-boiling material separation column and to control below 100 ppm the content of chloroprene in purified EDC to be fed to the thermal gas cracker.

As methods for overcoming the above problems to improve the efficiency of separation of chloroprene, there have been disclosed processes in which, (1) by introducing chlorine into a low-boiling material separation column or (2) by introducing a portion of a distillate from a low-boiling material separation column, chloroprene is chlorinated to convert it into a material having a higher boiling point than EDC and the high-boiling material is then separated in a high-boiling material separation column (Japanese Patent Application Laid-Open Nos. 61105/1979, 48127/1982 and 24968/1984; Japanese Patent Publication No. 61331/1982).

A further process is also disclosed in Japanese Patent Publication No. 16404/1974, in which low-boiling materials from a purification process of EDC are not drawn out but are fed together with EDC to a thermal cracker. According to this process, low-boiling materials in the form of a mixture of various unsaturated and saturated chlorinated hydrocarbons and benzol are converted into high-boiling materials when subjected in the presence of 1,2-dichloroethane to thermal cracking at 450°-650° C., especially at 500°-600° C. According to Examples 3 and 4 of the publication, the content of chloroprene in EDC to be fed to a thermal cracker is 400-1000 ppm.

The conventional techniques described above can solve some of the problems caused by chloroprene, but the following problems still remain unsolved.

Firstly, in a process for separating chloroprene by its chlorination, chlorine gas is introduced into a chlorination vessel or the like attached to a low-boiling material separation column or on the distillation side of the low-boiling material separation column. It is therefore necessary to use a chlorine-resistant material for the prevention of corrosion of the apparatus.

Further, not only low-boiling materials and chloroprene but also a portion of EDC are chlorinated, whereby high-boiling materials such as trichloroethane and the like are formed. EDC is thus consumed. This process is therefore economically disadvantageous. A process has hence been proposed, in which o-cresol or meta-cresol is added to improve the selectivity of chlorination to low-boiling materials so that chlorination of EDC can be prevented (Japanese Patent Publication No. 61331/1982). This process however requires advance preparation of the additive reagent into a solution. Additional facilities are also required, for example, to continuously charge the solution at a constant rate from a reservoir by means of a fixed displacement pump. This process is therefore disadvantageous in both the consumption of the additive reagent and economy and also cumbersome in operation.

In the process in which low-boiling materials are fed together with EDC to a thermal cracker without drawing them out from the purification step of EDC, the content of chloroprene in purified EDC to be obtained will be too high compared with the preferred level of not higher than 100 ppm (Japanese Patent Publication No. 16404/1974) so that it will be impossible to avoid coking of cracking tubes, inhibiting the cracking reaction, etc. over a long period of time.

Disclosure of the Invention

The present inventors have proceeded with an intensive investigation with a view toward achieving the above-described object, namely, removing chloroprene without blocking a low-boiling material separation column in a purification process of EDC so that EDC having a chloroprene content not higher than 100 ppm can be obtained. As a result, it has been found that chloroprene can be removed from EDC by subjecting chloroprene-containing EDC to heat treatment, leading to the completion of the present invention.

This invention therefore provides a process for the removal of chloroprene from 1,2-dichloroethane, which comprises subjecting chloroprene-containing 1,2-dichloroethane to heat treatment in the temperature range of from the boiling point (85° C.) of 1,2 dichloroethane to the thermal cracking temperature (300° C.) of 1,2-dichloroethane. Upon distillation of chloroprene-containing 1,2-dichloroethane in a fractionation column for the removal of low-boiling materials, at least a portion of a liquid distillate from the top thereof is subjected to heat treatment in the temperature range of from the boiling point of 1,2-dichloroethane to the thermal cracking temperature of 1,2-dichloroethane and at least a portion of the liquid distillate thus heat-treated is recycled to the fractionation column.

The preferred temperature range and treatment time of the heat treatment are 100°-250° C. and 30 minutes to 15 hours, respectively. Under these conditions, chloroprene can be effectively removed.

The finding that heat treatment of chloroprene-containing EDC in a manner as described above makes it possible to remove chloroprene has not been known as an industrially usable technique. It has been realized for the first time as a technique by the investigation of the present inventors.

Since chloroprene has high volatility (boiling point: 59.4° C.) and is prone to polymerization, depending on conditions such as temperature, concentration, etc., it therefore readily undergoes a polymerization reaction to form a polymer. Mere application of heat treatment cannot hence induce thermal cracking of chloroprene, so that it is difficult to remove chloroprene. It is for this reason that removal of chloroprene has heretofore been conducted by subjecting chloroprene to chlorination so as to raise the boiling point for higher stability.

In the present invention, chloroprene-containing EDC is basically subjected to heat treatment in the temperature range of from the boiling point (85° C.) of EDC to the thermal cracking temperature (300° C.) thereof, thereby making it possible to effectively remove chloroprene and hence to increase the concentration of EDC.

The following advantageous effects can be brought about by the process of the present invention.

(1) The present invention can remove chloroprene without consumption of chlorine gas as in the conventional processes.

(2) The conventional processes using chlorine gas result in the formation of high-boiling residue in a large quantity because of the chlorination. The present invention features the formation of high-boiling residue in a smaller quantity.

(3) A reduction in chloroprene and an increase in the unit of EDC are observed in the present invention. The content of chloroprene in purified EDC can be controlled at 50-95 ppm.

(4) The concentration of chloroprene is low in the low-boiling material separation column in this invention, thereby making it possible to avoid troubles such as blocking of the low-boiling material separation column due to polymerization of chloroprene.

(5) The content of chloroprene in purified EDC is low in this invention, so that coking of cracking tubes in a thermal cracker can be reduced and the cracking reaction can be conducted stably.

Figure 1:
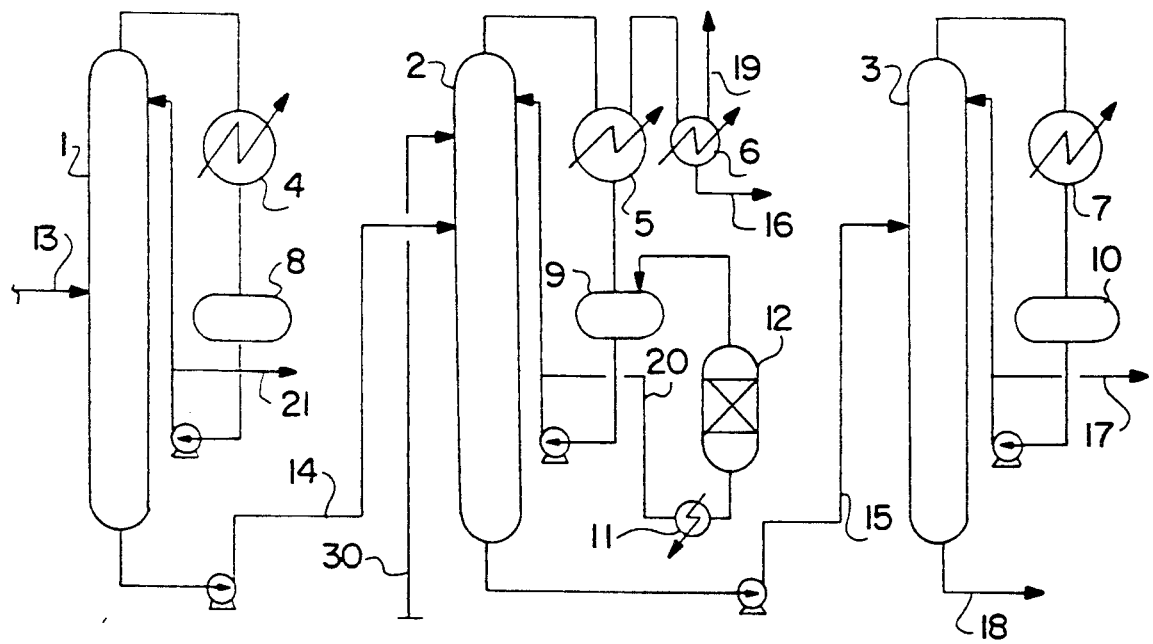
FIG. 1 is a flow chart showing one example of an EDC purification process according to the process of the present invention.

There are illustrated a dehydrating column 1, a low-boiling material separation column 2, and a high-boiling material separation column 3. Crude EDC is charged through line 13, while purified EDC is discharged as a distillate through line 17. Designated at 11 is a heater, and indicated at 12 is a heat treatment tank. There are also depicted condensers 4–7 and receivers 8–10.

BEST MODE FOR CARRYING OUT THE INVENTION

The process of the present invention is directed basically to the removal of chloroprene which is contained in EDC. Although no particular limitation is imposed on the mode for carrying out the process, the present invention can be applied as long as EDC contains chloroprene at a concentration of about 1-10wt.%, in other words, EDC contains chloroprene as an impurity. In the purification process of EDC by distillation, it is convenient to apply the above heat treatment in the low-boiling separation column because unnecessary low-boiling materials can also be removed together. In any case, it is necessary for the removal of chloroprene to apply sufficient heat treatment in the temperature range in which EDC remains stable, preferably at 100°-250° C. for 30 minutes to 15 hours, more preferably at 100°-150° C. for 1-10 hours. The heating time and period can however be determined suitably depending on intended EDC purity, means of the heat treatment, etc. Insufficient heat treatment cannot bring about sufficient effects. However, excessive heat treatment results in the formation of impurities (chlorinated hydrocarbons) in an increased quantity although the concentration of chloroprene may be lowered.

Typical embodiments of the present invention include that incorporated in a purification process of EDC which is used as a raw material for the production of vinyl chloride by the thermal cracking process.

A description will hereinafter be made of the present invention as applied to a process for the purification of EDC to be used in the production of vinyl chloride.

In this invention, the above-described problems of the conventional techniques can be overcome. Namely, it is possible to effectively remove chloroprene without its concentration to a high level in a low-boiling material separation column.

The present invention will now be described in detail with reference to the drawing.

FIG. 1 is a flow chart showing one embodiment of an EDC purification process which relies upon the process of the present invention.

In the drawing, it is possible to set, based on known techniques, the number of stages, the feed stage, the amount of bottom, the amount of liquid distillate, the reflux ratio and the like in each of the dehydrating column 1, low-boiling material separation column 2 and high-boiling material separation column 3 unless specifically referred to hereinbelow.

Firstly, crude EDC obtained by direct chlorination or oxychlorination of ethylene is introduced into the dehydrating column 1 through line 13. After water is separated out via line 21, it is fed to the low-boiling material separation column 2 through line 14. Unreacted EDC from the thermal cracking step, said unreacted EDC containing chloroprene and other thermal cracking byproducts, is also fed to low-boiling material separation column 2 via line 30.

Although crude EDC is usually free of chloroprene, unreacted EDC generally contains chloroprene at a concentration of 1000 ppm or higher. They are combined together and are fractionated in the low-boiling material separation column. Although the ratio of crude EDC to unreacted EDC is set in accordance with the efficiency of separation by the column, unreacted EDC is generally charged into the column at a stage higher than the feed stage for crude EDC. As an alternative embodiment, it is also possible to fractionate unreacted EDC alone in a fractionation column provided exclusively for unreacted EDC.

Next, chloroprene and other low-boiling materials are distilled out as vapor together with a portion of EDC through the top of low-boiling material separation column 2. EDC containing chloroprene is concentrated in condenser 5, and the resulting condensate (hereinafter called the "liquid distillate") is stored in receiver 9. The other low-boiling materials flow to condenser 6, where they are cooled. The resulting condensate is discharged through line 16, and uncondensed gas is discharged out of the system through vent 19.

It is desired to have the composition of vapor (hereinafter called the "distillate") which flows out from the top of low-boiling material separation column 2 containing approximately 20–40 wt.% of EDC and not more than 5 wt.% of chloroprene. This makes it possible to inhibit polymerization of chloroprene and to avoid blocking or the like of the column. It has heretofore been necessary to increase the concentration of chloroprene in the vapor to about 10 wt.% in order to improve the efficiency of separation of chloroprene. This naturally leads to the above-mentioned problem, i.e., the polymerization of chloroprene. The present invention has made it possible to realize sufficient removal of chloroprene by the below-described heat treatment in spite of the fact that the concentration of chloroprene in the top is controlled below 5 wt.% to avoid troubles which would otherwise occur by a polymerization reaction.

Low-boiling material separation column 2 is generally operated at a stage pressure of 1–2 kg/cm² and a distillation temperature of 50°–60° C.

A portion of chloroprene-containing EDC stored in receiver 9 is recycled to the top of low-boiling material separation column 2, said portion being called the "reflux", and the remainder is fed to heater 11 through line 20 so as to maintain a predetermined temperature. The remainder is then fed to heat treatment tank 12 and, after being held there for a predetermined time, is recycled back to receiver 9.

Chloroprene which is contained in EDC is subjected to heat treatment during the above step. As a result, there are observed a decrease of chloroprene and an increase of EDC.

By feeding steam or the like, heater 11 is controlled to raise the temperature of chloroprene-containing EDC to a predetermined heat treatment temperature in heat treatment tank 12. The heat treatment temperature is preferably 100°–250° C. more preferably 100°–150° C. The heat treatment time is preferably 30 minutes to 15 hours, with 1–10 hours being more preferred. The heat treatment time is determined by the amount to be treated, the capacity of the heat treatment tank and the heat treatment temperature. The pressure inside the heat treatment tank is controlled approximately at 2–15 kg/cm². Heat treatment methods include a preheating method such as heating by heater 11, a direct heating method in which heating is effected in the heat treatment tank, and an external heating method in which pump-assisted recirculation is conducted between a heater provided outside and the heat treatment tank.

The ratio of the remainder to the reflux may generally be from about 1:10 to about 1:30. If the proportion of the remainder is unduly small, thermal cracking of chloroprene cannot be effectively performed by the heat treatment. Any unduly large proportion of the remainder, however, results in the wasting of energy. As a modification, the reflux may be fed directly to the top from heat treatment tank 12 without feeding it back to receiver 9. In this modification, as long as the heat treatment is conducted under the same conditions, the thermal cracking of chloroprene is promoted further so that the concentration of chloroprene in the liquid to be recycled to the top is lowered further. Compared with the embodiment in which the liquid is recycled to receiver 9, there is the potential problem that the distillation column may be affected directly if chloroprene is polymerized in the heat treatment tank As another modification, the distillate from receiver 9 may be subjected in its entirety to heat treatment and may then be fed back wholly as a reflux to the top. In this case, cooling is needed once again after the heating, leading to a reduction in the heat efficiency.

Whichever embodiment or modification is employed, the distillate is subjected either partly or wholly to heat treatment. Since the amount of chloroprene in the distillate can be substantially reduced in this stage, the proportion of chloroprene in the liquid to be recycled to the top is lowered considerably to 2–4 wt.%. As a result, the concentration of chloroprene in the distillate from the top can be maintained below 5 wt.%. Accordingly, highly effective separation of chloroprene is feasible even when the reflux ratio (amount recycled-/amount fed) is smaller than the conventional processes.

Although the concentration of chloroprene in the EDC (bottom), from which chloroprene and other low-boiling materials have been removed, has already been reduced below 100 ppm, it still contains high-boiling materials at substantial concentrations. The EDC is drawn out from the bottom of low-boiling material separation column 2 and is fed to high-boiling material separation column 3 through line 15. After separation of the high-boiling materials, EDC is drawn out as purified EDC and is then fed to a thermal cracker through line 17. Since a portion of purified EDC is unreacted EDC, it will be utilized again. The high-boiling materials are discharged as a residue through line 18. In the manner described above, purified EDC containing not more than 100 ppm of chloroprene can be obtained. As a result, it is possible to avoid accelerated coking of cracking tubes in a thermal cracker and inhibition of the cracking reaction.

EXAMPLES

The present invention will be described further by the following examples. The present invention is however not limited by the following examples.

Example 1

Table 1 shows the material balance when the apparatus of FIG. 1 was operated without conducting the heat treatment. As a result, the concentration of chloroprene in the reflux was 8.5 wt.% so that highly effective fractionation of chloroprene in the low-boiling material separation column was realized. The concentration of chloroprene in purified EDC was reduced to as low as about 90 ppm by the above operation. Long-term operation under the above conditions, however, involves the potential problem that the low-boiling material separation column could be blocked.

Table 2 indicates the results of another operation in which a distillate from the low-boiling material separation column was subjected to heat treatment on the basis of the present invention.

The specification of the low-boiling material separation column was as follows:

| Inner column diameter: | 1.5 m |
| Column height: | 35 m |
| Stage pressure: | 1.2 kg/cm$^2$ |
| Distillation temperature: | 60° C. |
| Bottom temperature: | 100° C. |
| Reflux ratio: | 0.6 |

TABLE 1

| Stream No. | Flow rate (kg/hr) | | | |
|---|---|---|---|---|
| | EDC | CP | Miscellaneous | Total |
| 13 | 24,800 | 0 | 200 | 25,000 |
| 14 | 24,800 | 0 | 200 | 25,000 |
| 15 | 44,342 | 4 | 354 | 44,700 |
| 16 | 38 | 15 | 97 | 150 |
| 17 | 44,327 | 4 (90 ppm) | 219 | 44,550 |
| 18 | 15 | 0 | 135 | 150 |
| 19 | 20 | 11 | 119 | 150 |
| 20 | 280 (35%) | 68 (8.5%) | 452 | 800 |
| 30 | 19,600 | 30 (1500 ppm) | 370 | 20,000 |

CP Chloroprene
Miscellaneous: Other chlorinated hydrocarbons

TABLE 2

| Example | Treat. temp. °C. | Treat. time hr | Flow rate (kg/hr) | | |
|---|---|---|---|---|---|
| | | | EDC | CP | Misc. |
| Recycled liquid | — | — | 35.1 | 8.5 | 56.4 |
| Heat treatment 1 | 250 | 2 | 37.0 | 0.4 | 62.6 |
| Heat treatment 2 | 200 | 3 | 37.4 | 0.5 | 62.1 |
| Heat treatment 3 | 150 | 5 | 39.5 | 1.1 | 59.4 |
| Heat treatment 4 | 100 | 10 | 38.4 | 2.9 | 58.7 |

CP: Chloroprene
Misc.: Other chlorinated hydrocarbons

Example 2

Table 3 shows the material balance when the apparatus of FIG. 1 was operated while setting the operation conditions for the low-boiling material separation column as set out below. The operation was continued for additional 335 days. No blocking of the column was observed. The concentration of chloroprene in the reflux was 4 wt.%. The concentration of chloroprene in purified EDC was as good as 90 ppm.

| Stage pressure: | 1.2 kg/cm$^2$ |
| Distillation temperature: | 57° C. |
| Bottom temperature: | 100° C. |
| Reflux ratio: | 0.6 |
| Heat treatment: | 150° C. |

Note that only above 3 wt.% of the distillate was subjected to heat treatment.

TABLE 3

| Stream No. | Flow rate (kg/hr) | | | |
|---|---|---|---|---|
| | EDC | CP | Miscellaneous | Total |
| 13 | 24,788 | 0 | 200 | 24,988 |
| 14 | 24,788 | 0 | 200 | 24,988 |
| 15 | 44,342 | 4 | 354 | 44,704 |
| 16 | 26 | 7 | 97 | 132 |
| 17 | 44,327 | 4 (90 ppm) | 219 | 44,554 |
| 18 | 15 | 0 | 135 | 150 |
| 19 | 20 | 11 | 121 | 152 |
| 20 | 240 (30%) | 32 (4%) | 528 | 800 |
| 30 | 19,600 | 30 (1500 ppm) | 370 | 20,000 |

CP Chloroprene
Miscellaneous: Other chlorinated hydrocarbons

Comparative Example 1

Table 4 indicates the material balance when the apparatus of FIG. 1 was operated without heat treatment while setting the operation conditions of the low-boiling material separation column as described below. The concentration of chloroprene in the reflux was as high as 11 wt.%, so that the effects of the fractionation were high. The concentration of chloroprene in purified EDC was as good as 90 ppm. When the operation was continued for additional 67 days, blocking of the column was observed so that the operation was suspended. This was caused by the unduly high concentration of chloroprene in the reflux.

| Stage pressure: | 1.2 kg/cm$^2$ |
| Distillation temperature: | 57° C. |
| Bottom temperature: | 100° C. |
| Reflux ratio: | 0.8 |
| Heat treatment: | No applied |

TABLE 4

| Stream No. | Flow rate (kg/hr) | | | |
|---|---|---|---|---|
| | EDC | CP | Miscellaneous | Total |
| 13 | 24,794 | 0 | 200 | 24,994 |
| 14 | 24,794 | 0 | 200 | 24,994 |
| 15 | 44,342 | 4 | 354 | 44,700 |
| 16 | 29 | 19 | 97 | 145 |
| 17 | 44,327 | 4 | 219 | 44,550 |
| 18 | 15 | 0 | 135 | 150 |
| 19 | 23 | 7 | 119 | 149 |
| 20 | — | — | — | — |

TABLE 4-continued

| Stream No. | Flow rate (kg/hr) | | | |
|---|---|---|---|---|
| | EDC | CP | Miscellaneous | Total |
| 30 | (30%)* 19,600 | (11%)* 30 (1500 ppm) | 370 | 20,000 |

CP Chloroprene
Miscellaneous Other chlorinated hydrocarbons
*In reflux

INDUSTRIAL APPLICABILITY

As has been described above, the process of the present invention for the removal of chloroprene can be applied to a system in which chloroprene is contained as an impurity in EDC. From the viewpoint of diversification of technology, the present invention can be used practically in all the industrial fields in which chlorination is employed, as a substitute for the conventional chlorination processes.

In particular, the present invention can be applied suitably to the technical field in which vinyl chloride is produced from thermal cracking of EDC. Since the stability of production of vinyl chloride can be improved and unreacted EDC can be used effectively as a raw material, the economy of production can be improved.

We claim:

1. A process for the removal of chloroprene from 1,2-dichloroethane, which comprises subjecting chloroprene-containing 1,2-dichloroethane to heat treatment at a temperature in the range of from the boiling point of 1,2-dichloroethane to the thermal cracking temperature of 1,2-dichloroethane without the use of a catalyst, whereby the chloroprene is thermally cracked.

2. The process of claim 1, wherein the temperature of the heat treatment ranges from 100° C. to 250° C.

3. The process of claim 1, wherein the time required for the heat treatment is from 30 minutes to 15 hours.

4. A process for the removal of chloroprene from 1,2-dichloroethane, which comprises, the steps of distilling the chloroprene-containing 1,2-dichloroethane in a fractionation column adapted for the removable of low-boiling materials to produce a distillate comprising a liquid distillate at the top of the column, subjecting at least a portion of the liquid distillate from the top of the column to a heat treatment without the use of a catalyst, at a temperature in the range of from the boiling point of 1,2-dichloroethane to the thermal cracking temperature of 1,2-dichloroethane and then recycling at least a portion of the thus heat-treated liquid distillate to the fractionation column.

5. The process of claim 4, wherein the temperature of the heat treatment ranges from 100° C. to 250° C.

6. The process of claim 4, wherein the time required for the heat treatment is from 30 minutes to 15 hours.

7. The process of claim 4, wherein the concentration of chloroprene contained in the distillate from the factionation column is not higher than 5 wt.%.

8. A process for the removal of chloroprene from 1,2-dichloroethane by distillation of the chloroprene-containing 1,2-dichloroethane, which comprises conducting the distillation in a fractionation column adapted for the removal of low-boiling materials, subjecting at least a portion of a liquid distillate obtained from the top of the column to heat treatment at a temperature in the range of from the boiling point of 1,2-dichloroethane to the thermal cracking temperature of 1,2-dichloroethane, recycling the thus-heat treated liquid distillate to the liquid distillate from the top of the column, and then recycling at least a portion of the thus-produced liquid distillate mixture to the fractionation column.

9. The process of claim 8, wherein the temperature of the heat treatment ranges from 100° C. to 250° C.

10. The process of claim 8, wherein the heat treatment is conducted for from 30 minutes to 15 hours.

* * * * *